United States Patent
De Jonge

(10) Patent No.: US 9,966,223 B2
(45) Date of Patent: *May 8, 2018

(54) DEVICE FOR CORRELATIVE SCANNING TRANSMISSION ELECTRON MICROSCOPY (STEM) AND LIGHT MICROSCOPY

(71) Applicant: LEIBNIZ-INSTITUT FUER NEUE MATERIALIEN GEMEINNUETZIGE GMBH, Saarbruecken (DE)

(72) Inventor: Niels De Jonge, St. Ingbert (DE)

(73) Assignee: Leibniz-Institut Fuer Neue Materialien gemeinnuetzige GmbH, Saarbruecken (DE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/124,697

(22) PCT Filed: Mar. 10, 2015

(86) PCT No.: PCT/DE2015/100097
§ 371 (c)(1),
(2) Date: Sep. 9, 2016

(87) PCT Pub. No.: WO2015/135534
PCT Pub. Date: Sep. 17, 2015

(65) Prior Publication Data
US 2017/0018399 A1    Jan. 19, 2017

(30) Foreign Application Priority Data
Mar. 12, 2014    (DE) .................. 10 2014 103 360

(51) Int. Cl.
*H01J 37/22*    (2006.01)
*G02B 21/34*    (2006.01)
(Continued)

(52) U.S. Cl.
CPC ............ *H01J 37/228* (2013.01); *G02B 21/02* (2013.01); *G02B 21/06* (2013.01); *G02B 21/18* (2013.01);
(Continued)

(58) Field of Classification Search
CPC ........ H01J 37/228; H01J 37/244; H01J 37/26; H01J 2237/2443; H01J 2237/24455;
(Continued)

(56) References Cited

U.S. PATENT DOCUMENTS

| 4,990,776 A | 2/1991 | Fushimi et al. |
| 5,811,804 A | 9/1998 | Van Blitterswijk et al. |

(Continued)

FOREIGN PATENT DOCUMENTS

| WO | 2004020453 A1 | 3/2004 |
| WO | 2010/120238 A1 | 10/2010 |

(Continued)

OTHER PUBLICATIONS

International Search Report of PCT/DE2015/100097, dated Jul. 10, 2015.
(Continued)

*Primary Examiner* — Nicole Ippolito
(74) *Attorney, Agent, or Firm* — Collard & Roe, P.C.

(57) ABSTRACT

The invention relates to a device for correlative scanning transmission electron microscopy (STEM) and light microscopy. In order to create a device for correlative microscopy which enables an improved combination of light microscopy and STEM methods, a STEM detector (7) according to the invention is combined with a photo-optical lens (8). This detection device combines the efficient detection by means of STEM microscopy of materials having a high atomic
(Continued)

number, for example specific nanoparticle markers in a specimen in a liquid, such as a cell, with simultaneous light microscopy.

13 Claims, 4 Drawing Sheets

(51) Int. Cl.
*H01J 37/26* (2006.01)
*G02B 21/18* (2006.01)
*H01J 37/244* (2006.01)
*G02B 21/02* (2006.01)
*G02B 21/06* (2006.01)
*B82Y 5/00* (2011.01)

(52) U.S. Cl.
CPC ............ *G02B 21/34* (2013.01); *H01J 37/244* (2013.01); *H01J 37/26* (2013.01); *B82Y 5/00* (2013.01); *H01J 2237/2443* (2013.01); *H01J 2237/24455* (2013.01); *H01J 2237/2802* (2013.01); *Y10S 977/927* (2013.01)

(58) Field of Classification Search
CPC . H01J 2237/2802; G02B 21/02; G02B 21/34; G02B 21/06; G02B 21/18; B82Y 5/00
USPC .................. 250/306, 307, 309, 310, 311, 397
See application file for complete search history.

(56) References Cited

U.S. PATENT DOCUMENTS

| 8,604,429 | B2 | 12/2013 | Yaguchi et al. |
| 2007/0249064 | A1 | 10/2007 | De La Fuente et al. |
| 2011/0284745 | A1 | 11/2011 | Nishiyama et al. |
| 2012/0025103 | A1 | 2/2012 | Deshmukh et al. |
| 2012/0120226 | A1 | 5/2012 | De Jonge |
| 2012/0182548 | A1 | 7/2012 | Harb et al. |
| 2012/0292505 | A1 | 11/2012 | Damiano et al. |
| 2013/0200262 | A1 | 8/2013 | Kruit et al. |
| 2014/0246583 | A1 | 9/2014 | Ominami et al. |
| 2015/0034822 | A1* | 2/2015 | Reinhorn ............... H01J 37/244 250/307 |
| 2015/0214001 | A1 | 7/2015 | Buijsse |
| 2015/0293084 | A1 | 10/2015 | Del Pino Gonzalez De La Higuera et al. |
| 2017/0191995 | A1* | 7/2017 | De Jonge ............... B82Y 15/00 |
| 2017/0205363 | A1* | 7/2017 | De Jonge ........... G01N 23/2251 |

FOREIGN PATENT DOCUMENTS

| WO | 2013/151421 A2 | 10/2013 |
| WO | 2014/007624 A1 | 1/2014 |
| WO | 2014016465 A1 | 1/2014 |

OTHER PUBLICATIONS

A. C. Zonnevylle et al., "Integration of a high-NA light microscope in a scanning electron microscope," Journal of Microscopy, vol. 252, Issue 1, 2013, pp. 58-70.
Nalan Liv et al., "Simultaneous Correlative Scanning Electron and High-NA Fluorescence Microscopy," PLOS ONE, Feb. 2013, vol. 8, Issue 2, e55707, total of 10 pages.
International Search Report of PCT/DE2015/100245, dated Oct. 13, 2015.
International Search Report of PCT/DE2015/100238, dated Oct. 27, 2015.
Diana B Peckys et al: "Liquid Scanning Transmission Electron Microscopy: Imaging Protein Complexes in their Native Environment in Whole Eukaryotic Cells" Microscopy and Mircoanalysis, Springer, New York, US, vol. 20, No. 2, Apr. 1, 2014, pp. 346-365.
Elisabeth A Ring et al: "Microfluidic System for Transmission Electron Microscopy", Microscopy and Microanalysis, Springer, New York, US, vol. 16, No. 5, Oct. 1, 2010, pp. 622-629.
Kyoung, Lee et al: "Rapid Detection of Intracellular Nanoparticles by Electron Microscopy", Journal of Analytical Science & Technology, vol. 1, No. 1, Jan. 1, 2010, pp. 71-73.
Watanabe, Shigeki et al: "Protein localization in electron micrographs using fluorescence nanoscopy", Nature Methods, vol. 8, No. 1, Jan. 2011, pp. 1-18.

\* cited by examiner

DEVICE FOR CORRELATIVE SCANNING TRANSMISSION ELECTRON MICROSCOPY (STEM) AND LIGHT MICROSCOPY

CROSS REFERENCE TO RELATED APPLICATIONS

This application is the National Stage of PCT/DE2015/100097 filed on Mar. 10, 2015, which claims priority under 35 U.S.C. § 119 of German Application No. 10 2014 103 360.4 filed on Mar. 12, 2014, the disclosures of which are incorporated by reference. The international application under PCT article 21(2) was not published in English.

The invention relates to a device for correlative scanning transmission electron microscopy (STEM) and light microscopy.

Observation of processes, compositions and structures in biological specimens containing a liquid phase is difficult in the nanometer range. Examples of specimens of this kind include protein complexes in eukaryotic cells, lipid vesicles in solution or in cells, or cellular-material structures. A resolution of approximately 200 nm can be achieved with standard light microscopes and of 20 to 30 nm with special light-microscopy techniques. X-ray microscopes are in so far problematic as suitable x-ray sources require complicated equipment. Scanning-probe techniques are only suitable for investigating surfaces. Electron microscopy is the traditional technique used for nano-range investigations but requires a vacuum for the electron optics, making the investigation of specimens in liquid impossible. The past few years have accordingly seen the development of techniques to carry out electron microscopy in liquids. As a rule, the liquid is enclosed in a chamber with a thin, electron-permeable window. The use of scanning transmission electron microscopy (STEM) to achieve nanometer-range resolution of nanoparticles with high high atomic numbers, for example gold nanoparticles, in thick layers of liquids having low atomic numbers, for example water, is particularly advantageous. Nanoparticles are often used as a specific protein label for investigating cell processes.

Although a high level of resolution is usually obtainable, the specimen chamber is limited to a few micrometers if a resolution of a few nanometers is desired.

Another approach is the use of environmental scanning electron microscopy (ESEM). Specimens in a liquid, such as water, are cooled down to a few degrees Celsius and then kept at low pressure in water vapour. The pressure may be adjusted such as to maintain a balance between the liquid and the vapour, thereby making it possible to observe a specimen in a thin layer of water. Detection is typically via the secondary-electron detector, although this approach is only possible for the surface of the specimen. Observation of layer thicknesses of up to a hundred nanometers within the specimen is possible with a backscattered-electron detector. However, this last detection method is relatively inefficient and, on account of the radiation damage, not usable for examining native cell material. Cells have to be fixed and stained with metal in order for them to withstand the radiation damage and for sufficient contrast to be produced during imaging. The STEM detector provides a much more efficient method of detecting specific markers consisting of nanoparticles with high atomic numbers in the spread-out cell regions. Nanoparticle markers can be detected efficiently in whole cells by means of STEM, and sample preparation is minimal.

The combination of light microscopy and electron microscopy, correlative microscopy as this combination is termed, is of particular interest. Cell processes and cell structures are observed by way of light microscopy, which has limited resolving power, while high-resolution electron microscopy is used at certain points in time and in certain regions. Electron beams usually damage biological material. Regions and points in time that are of particular interest are accordingly selected by light microscopy because it will not damage the specimen. Light microscopy also provides important information to supplement electron microscopy. For example, it can provide general images of the cells and information as to the existence of certain proteins in certain cell regions, for example through the use of specific fluorescent markers. Examples of markers include genetically engineered markers such as green-fluorescent proteins or markers doped with fluorescent atoms of high atomic number, for example, those referred to as "quantum dots". In principle, light-microscopy images are taken with other devices than those used for electron microscopy, meaning that the temporal correlation is lost and each imaged region has to be localized.

It would be extremely useful if both microscopy methods could be carried out within the same system, so that observations of processes and structural information are temporally correlated to the greatest degree possible via both methods simultaneously and errors in the localization of regions or the modification of structures over time are avoided.

One way of accomplishing this consists in a combined fluorescent microscope, which is attached to a high-voltage transmission electron microscope (TEM) or a STEM column. Temporal correlation in the range of approx. 30 seconds is achieved by rotating the specimen between the vertical electron beam and the light beam. Another approach is to integrate an optical lens in an ESEM microscope and detect the electron backscattering. This method, however, is relatively inefficient and is poorly suited for use with sensitive biological specimens on account of the radiation damage.

The objective of the present invention consists in the creation of a device for correlative microscopy according to the preamble, with which light-microscopy and STEM methods can be combined better.

This objective is established with the device according to the invention in that it combines a STEM detector with a photo-optical lens.

This detection device combines efficient STEM-microscopy detection of materials with high atomic numbers, for example specific nanoparticle markers in a specimen contained in a liquid, such as a cell, with simultaneous light microscopy, for example via fluorescence contrast of fluorescent protein markers in cells or via scatter contrast of the cell material. The invention differs in so far from the prior art as it enables highly efficient detection, with the maximum possible resolution, of materials with high atomic numbers in the specimen and fully temporally correlated light microscopy. A specimen may either be dried, embedded in a thin layer of liquid or embedded in a layer of ice.

A preferred embodiment of the invention consists in that the STEM detector is integrated in a photo-optical lens.

In this context, it is to advantage that the STEM detector is positioned in a cavity in the photo-optical lens.

The invention makes provision for the cavity to have, at the specimen end, a small-diameter opening followed by a conical electron drift chamber at the bottom end of which the STEM detector is located.

"Bottom" refers here to an electron beam direction from top to bottom. Arbitrary beam directions are possible depending on how the device is set up. This means that the opening is located at the lens end which is nearer the specimen holder. Following on from the opening is the conical electron drift chamber, which widens out in the downward direction. The STEM detector is located at the bottom end of the electron drift chamber.

It is within the scope of the invention that the STEM-detector signal can be transmitted to the outside at the side of the lens.

The invention provides for a specimen holder to be located at that end of the photo-optical lens which is nearer a specimen.

In this connection, provision is made for the specimen holder to be configured as a thin, electron-permaeable membrane.

Since the electron beam passes through the specimen mounted on the specimen holder, the specimen holder must be electron-permeable.

It is also within the scope of the invention that the electron drift chamber and the space surrounding the specimen holder have the property of being able to establish a vacuum.

It must be possible to generate a vacuum in the area surrounding the specimen and in the electron drift chamber.

The invention also provides for an electron beam source to be located on the other side of the specimen holder from the STEM-detector.

According to the invention, furthermore, a light source and photo-optical detection means are connected to the lens.

The lens with the integrated STEM detector may be installed in different kinds of electron microscopes, e.g. an ESEM with typical electron energy of 30 keV or a high-resolution STEM with typical electron energy of 200 keV.

It is within the scope of the invention to provide one or a plurality of other photo-optical beam paths for detection or illumination purposes.

A further embodiment of the invention provides for the light source to be fitted at the side of the STEM detector, the focus of the light beam to overlap with the electron beam and a photo-optical detection path to overlap with the illumination beam.

It is also possible to position the STEM detector between the optical lens and the specimen. In the same way, it is possible for the STEM detector to be movable in the area between the optical lens and the specimen.

It is within the scope of the invention for the STEM detector to have one or more than one detection surface, at least one of which captures a principal beam and at least another of which captures scattered electrons.

According to the invention, finally, the STEM detection surfaces are located inside, above or to the side of the photo-optical lens, but on the opposite side of the specimen to the side facing the electron source.

One possible field of application for the invention is the investigation of cell processes based on the dynamic anabolism and catabolism of protein complexes. A combination of different nanoparticles is used to detect a wide range of different proteins which are combined with various protein-specific fluorescent markers. A specific research area may take the form of biomedical research, for example, in particular cancer research. Another possible field of application for the invention is the investigation of the interaction of nanomaterials with cells; general images of whole cells may be obtained and fluorescent markers used to identify areas with certain proteins, specific organelles, lipids, DNA, etc. Other fields of application include pathology, forensic medicine, the investigation of marine organisms and the imaging of bacteria and viruses. Diagnosing the presence of specific proteins or other macromolecules and of accumulations of certain proteins and macromolecules, for example to detect cancer in cell material, constitutes another possible application of the invention.

A further possible application of the invention is the investigation of specimens from other fields, for example the material sciences, where a combination of light microscopy and electron microscopy is required. An example here is the field of energy storage using battery materials. Other possible fields of application include the investigation of polymers, the characterization of nanoparticles, the testing of precision tools and the imaging of various materials, for example fragments of corroded steel pipes.

Some embodiments of the invention are explained below by reference to drawings.

The drawing in

Figure 1:
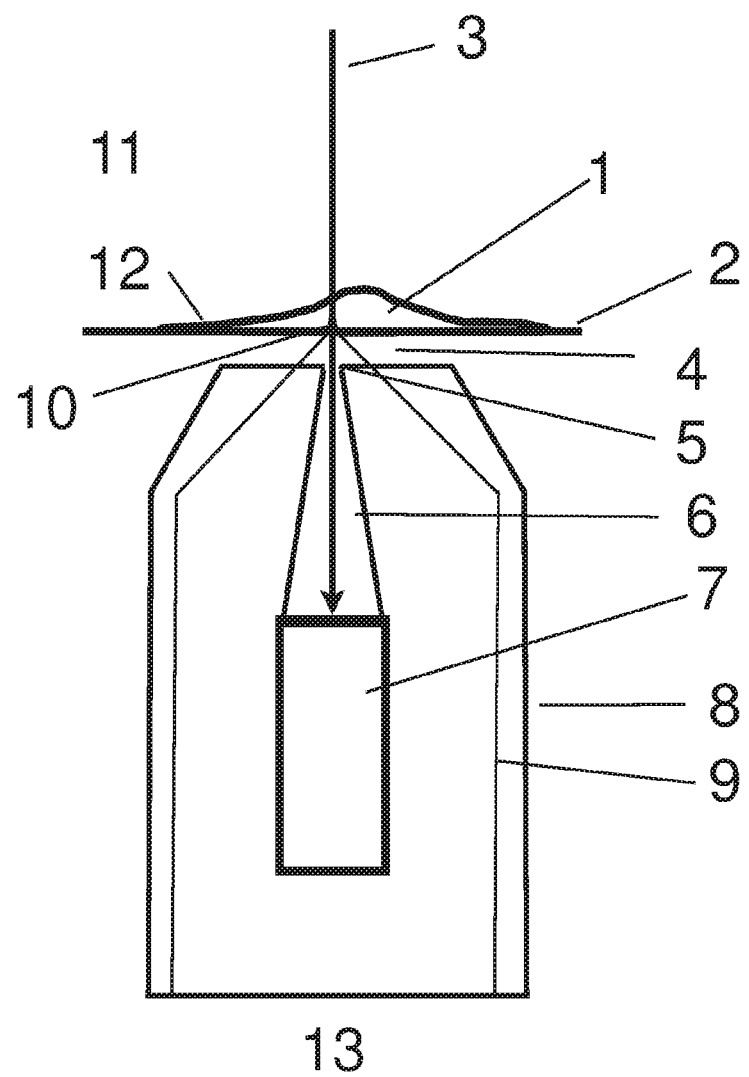
FIG. 1 is a schematic diagram of a detection device according to the invention.

FIG. 1 shows a detection device for correlative scanning transmission electron microscopy and light microscopy. A specimen (1), for example a eukaryotic cell (1), is in place on a thin, electron-permeable membrane (2). The membrane (2) is connected to a specimen holder. The specimen (1) is imaged with an electron beam (3), the specimen (1) typically being scanned with an electron beam (3). Transmitted electrons propagate through the membrane (2), across a gap (4), into an electron drift chamber (6) within a cavity with a small opening (5), to the STEM detector (7). The electron drift chamber (6) and the STEM detector (7) are located in a cavity in the photo-optical lens (8). The lens (8) focuses a broad light beam (9) onto the specimen (1) at a focal point (10). The specimen (1) and the electron drift chamber (6) are surrounded by a vacuum (11). A thin layer of liquid (12) covers the specimen (1). The photo-optical detection means and the light source are located in the area (13) beneath the lens (8).

The procedure according to the invention is as follows:

A specimen (1) in a liquid, for example a eukaryotic cell, is in place on a thin membrane (2) in the electron microscope. The membrane (2) consists of lightweight materials of low atomic number, for example carbon nitride or silicon nitride, enabling an electron beam (3) of sufficient energy, for example 30 keV or 200 keV, to permeate said membrane (2).

The membrane (2) is supported by a carrier, e.g. a silicon microchip or a thin material. The carrier is disposed on a specimen holder having means to move in the x, y and z directions.

The electron beam (3) is configured such that the beam runs from the top end to the bottom end of the microscope and through the specimen (1). The electron beam may of course run in another direction instead of from top to bottom, for example from bottom to top or from left to right.

A special optical lens (8) is positioned beneath the membrane (2). The optical path is configured such that the light passes through the lens (8) and is focused onto the specimen, while reflected or fluorescent light is collected by the same lens (8) and routed to the detector, for example by using an optical filter cube consisting of dichroic mirrors. The light beam converges toward the specimen (1) with a semi-aperture angle of, for example, 0.75 rad, said angle being defined by the numerical aperture of the lens (8). A high-resolution air or vacuum lens provides 100-fold magnification in the case of a numerical aperture of 1.0 and a working distance of 0.15 mm. The lens (8) focuses the light beam (9) onto the specimen (1). At the other end of the lens (8) the light beam (9) is broad, with a diameter of, for example, 9 mm. The lens (8) has a conical recess which is located along the optical axis of the lens (8) and serves as electron drift chamber (6). The dimensions of the conical recess are suited to the beam path used for STEM detection, with typical semi-aperture angles of 0.050 to 0.20 rad. At the top end of the lens (8), directly beneath the specimen (1), the diameter of the recess is, for example, 0.060 mm. It decreases by 0.20 rad over a distance of 0.15 mm. The recess extends through the lens (8) at an angle of 0.2 rad. At the bottom end of a lens (8) of 10 mm length the diameter of the recess is thus 4.0 mm. The STEM detector (7) is positioned at the widest point of the recess.

Although the presence of the recess limits the optical path through the lens (8), it only reduces the overall amount of light passing through the lens. The lens (8) is still able to focus the light beam onto the specimen (1), collect light from the specimen and project a magnified image of the illuminated area onto a position-sensitive light detector for purposes of light microscopy. A confocal optical system may be used as an alternative. Alternatively, it is also possible to use a plurality of photo-optical beam paths for purposes of detection or illumination.

The STEM detector consists of a cylinder of scintillator material, having a diameter of, for example, 4.0 mm, for converting electrons into light pulses. The scintillator is coupled with a sensitive light detector, for example a multiplier phototube. This tube is connected to the side of the lens. For this purpose, the scintillator has a connection surface at the side of the optical lens. The outside is provided with reflective, slightly stepped material so as to prevent light from the photo-optical beam path from being coupled into the STEM detector (7). The STEM detector (7) may also consist of a small microchip with a charge-coupled device detector. The central disc of the STEM detector (7), with an appropriate half-angle of 50 mrad, is decoupled from detection, for example blocked, or the signal from this area is used as secondary detection signal. The STEM detector (7) accordingly registers signals from transmitted electrons with half-angles of 50 mrad to 0.20 rad. The signal is referred to as the dark field signal.

Figure 2:
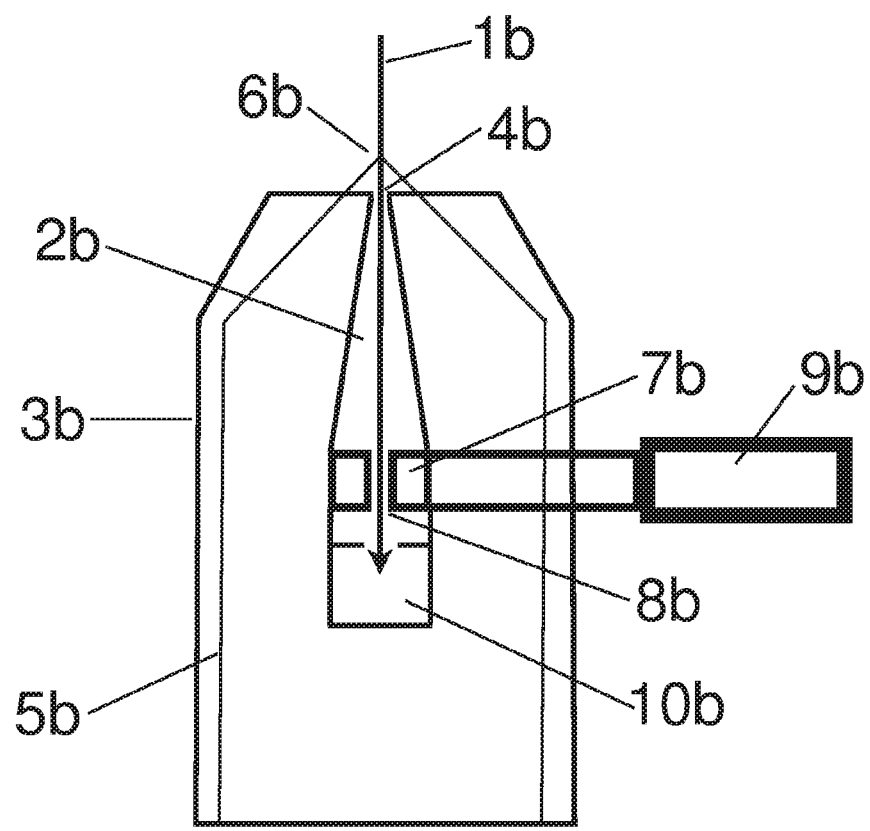
FIG. 2 shows a schematic detail of the detection device for correlative scanning transmission electron microscopy and light microscopy.

FIG. 2 shows a schematic detail of the detection device for correlative scanning transmission electron microscopy and light microscopy. An electron beam (1b) transmitted through a specimen (not shown here) enters an electron drift chamber (2b) located in a cavity in a photo-optical lens (3b). The electron drift chamber is accessible through a small opening (4b). The lens (3b) focuses a broad light beam (5b) on a focal point (6b). Within the electron drift chamber (2b) there is a STEM detector (7b), which is made of a rod of scintillating material so that electrons are converted into light pulses. The rod (7b) has an aperture (8b) so that electrons in the bright field pass through the detector unhindered and only electrons scattered by a given minimum angle are detected. The rod-shaped STEM detector (7b) extends out of the lens (3b) at the side thereof and is connected to a light-sensitive light detector such as a photoelectron multiplier or a photodiode (9b) in order to convert the light into an electric signal. Instead of a rod of scintillating material and a light detector, it is also possible to use another electron detector, such as a semiconductor electron detector, which is of comparable size. Electrons in the bright field are captured in a separate chamber with a small aperture stop (10b) so that they do not interfere with the STEM signal.

In a further embodiment, the STEM detector is not mounted within the optical lens but in the vicinity of the optical lens. The STEM detector captures the electron beam. The photo-optical beam is guided in such a way that the focus of the beam overlaps with the electron beam but otherwise runs at the side thereof. The STEM detector may be positioned at the side of and in contact with the photo-optical lens. The photo-optical system may consist of a plurality of beam paths and lenses.

Figure 3:
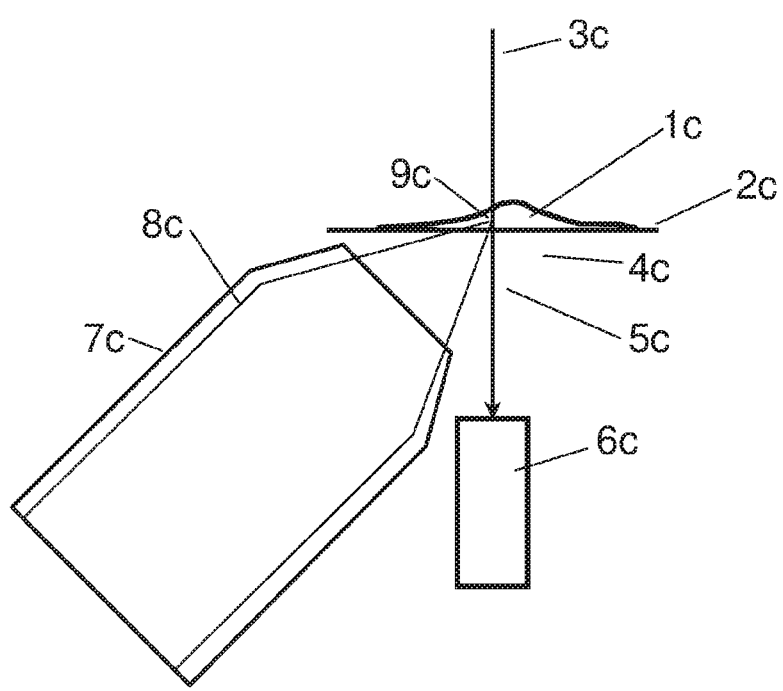
FIG. 3 is a schematic diagram of another embodiment of the detection device according to the invention.

FIG. 3 shows a further embodiment of a detection device for correlative scanning transmission electron microscopy and light microscopy. A specimen (1c), for example a eukaryotic cell (1c), is in place on a thin, electron-permeable membrane (2c). The membrane (2c) is connected to a specimen holder. The specimen (1c) is imaged with an electron beam (3c). Electrons propagate through the membrane (2c) and run in the vacuum beneath the membrane (4c). The transmitted electron beam (5c) propagates further to the STEM detector (6c). A photo-optical lens (7c) is positioned at the side of the electron beam (5c). The lens (7c) focuses a broad light beam (8c) onto the specimen (1c) at a focal point (9c). The photo-optical detection means and the light source are located beneath the lens (7c).

In a further embodiment, a thin STEM detector is positioned between the photo-optical lens and the specimen. Depending on how the STEM detector is configured, the light signal and the STEM signal may be detected in quick succession, with photo-optical detection taking place as soon as the STEM detector is moved out of the photo-optical beam path.

In another embodiment, the STEM detector is not symmetric but has one or more than one detection surface; at least one of these detection surfaces captures the scattered electrons. The detection surfaces may be provided within, above or at the side of the photo-optical lens. The light signal and the STEM signal may be detected simultaneously.

Figure 4:
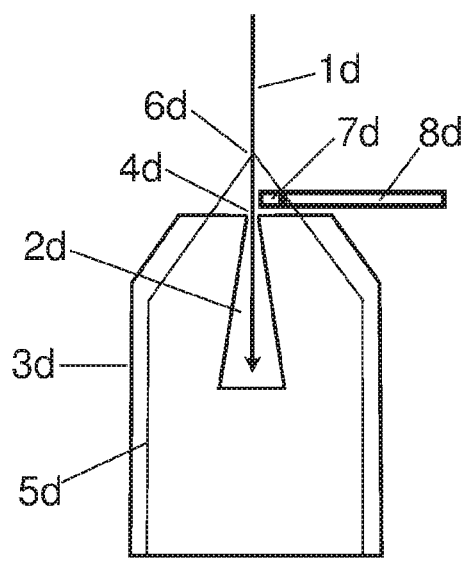
FIG. 4 shows a schematic detail of another embodiment of the detection device for correlative scanning transmission electron microscopy and light microscopy.

FIG. 4 shows a schematic detail of another embodiment of the detection device for correlative scanning transmission electron microscopy and light microscopy. An electron beam (1d) being transmitted through a specimen (not shown here) is captured in a cavity (2d) in a photo-optical lens (3d). The cavity (2d) is accessible through a small opening (4d). The lens (3d) focuses a broad light beam (5d) onto the specimen at a focal point (6d). A STEM detection surface (7d) is located between the focal point (6d) and the upper edge of the lens with the small opening (4d). The STEM detection surface (7d) may be made of a rod of scintillating material and this rod is connected to a light detector (8d). A semiconductor electron detector may also be used.

A typical application for a method according to the invention is described below. A eukaryotic cell such as a COS7 fibroblast cell is used by way of example. The cell contains nanoparticles, for example gold nanoparticles of 5 nm diameter. The nanoparticles have a coating for specific binding of the nanoparticle to a protein, for example a coating containing a molecule with epidermal growth factors. This molecule is a ligand for the receptor for epidermal growth factors. Detection of this receptor is important for research on and diagnosis of certain forms of cancer, for example breast cancer. The cell is immobilized in liquid on a supporting membrane and examined by means of light microscopy. Moving the specimen holder enables different cell regions to be examined. The focus is adjusted by moving the cell in the z direction. At a certain point in time, nanoparticles are applied to the specimen, which undergoes continued examination by light microscopy. If an area is particularly interesting, the air surrounding the specimen is suctioned off, for the most part by means of a vacuum pump, and the temperature of the specimen is lowered to a few degrees Celsius. The pressure is then regulated such that vaporous and liquid water are in equilibrium. This procedure makes it possible to keep the specimen covered with a thin film of water, while the inside of the cell contains water. In certain cases the cell material may be fixed, for example with glutaraldehyde, and the liquid replaced by pure water. The electron beam is then switched on and the specimen scanned therewith. The electron beam is a thin, converging beam with a typical half-angle of 5 mrad, and it is directed at a particularly interesting point on the specimen. A contrast is generated on the cell material due to scattering of the electron beam. Scattered electrons and electrons in a cone with a semi-aperture angle of 0.20 mrad enter the drift chamber and pass to the detector. The signals at least of the electrons with half-angles between 50 mrad and 0.20 rad are collected with the STEM detector. The electron beam is scanned over the specimen pixel by pixel, and the STEM signal stored. Using STEM, one achieves nanometer-range resolution, a high contrast level with markers of high atomic number and a lower level of resolution in the area of the cell material. The photo-optical beam is used simultaneously to illuminate the specimen and to collect either scattered or fluorescent light. Light microscopy may also be used subsequent to STEM detection in order to examine the cell after it has been exposed to the electron beam and to investigate other cell regions.

The scope of the present invention includes a method of examining a specimen by means of light and electron microscopy, where the light and electron beams are spatially and temporally connected, i.e. correlated. To this end, the specimen is first mounted on a thin carrier and this is traversed in the x, y and z directions until the desired position relative to the electron beam is reached. The spatial positioning of the electron beam, the light beam and the specimen are known to the highest degree of accuracy, meaning that the images are also very accurately correlated spatially. The device is precisely dimensioned for this purpose. The spatial relation or correlation of the beam paths may additionally be calibrated, for which purpose images of easily recognizable objects are used. The correlation of the beam paths may be determined therefrom and the stored information used to determine the spatial relation of images of specimens under investigation. Once the images have been taken, they are stored in an image file, for example, and can then be coupled with the spatial correlation data. Light- and electron-microscopy images may either be depicted separately or be superimposed within one and the same coordinate system so as to obtain an overall image of the specimen.

The invention also includes a method which enables the light- and electron-microscopy images to be correlated temporally. To this end, for example, the light- and electron-microscopy images are taken simultaneously or almost simultaneously and their point in time and duration of take are measured or calculated. For example, the two images obtained by light- and electron microscopy are stored and, at the same time, so are the times of the takes. The images may also be taken in a certain sequence, e.g. two light-microscopy images and one STEM image. The images may also be taken repetitively. For example, 100 light-microscopy images may be taken, with short pauses between them, while, during the same period, seven STEM images are taken. In this method, the images are stored together with the points in time and duration of the takes, thereby making it possible to depict the images in temporal correlation.

The invention claimed is:

1. Device for correlative scanning transmission electron microscopy (STEM) and light microscopy, wherein a STEM detector is combined with a photo-optical lens, wherein the STEM detector is integrated in a photo-optical lens, and wherein the STEM detector is positioned in a cavity in the photo-optical lens.

2. Device according to claim 1, wherein the cavity has, at the specimen end, a small-diameter opening followed by a conical electron drift chamber at the lower end of which the STEM detector is located.

3. Device according to claim 1, wherein the signal from the STEM detector can be transmitted to the outside at the side of the lens.

4. Device according to claim 1, wherein a specimen holder is located at that end of the photo-optical lens which is nearer to a specimen.

5. Device according to claim 4, wherein the specimen holder is configured as a thin, electron-permeable membrane.

6. Device according to claim 4, wherein an electron drift chamber of the cavity and the space surrounding the specimen holder have the property of being able to establish a vacuum.

7. Device according to claim 4, wherein an electron beam source is located on the other side of the specimen holder from the STEM detector.

8. Device according to claim 4, wherein the STEM detector is positioned between the optical lens and the specimen.

9. Device according to claim 1, wherein a light source and photo-optical detector are connected to the lens.

10. Device according to claim 9, wherein the light source is fitted at the side of the STEM detector, the focus of the light beam overlaps with the electron beam and the photo-optical detection path overlaps with the illumination beam.

11. Device according to claim 1, wherein one or a plurality of other photo-optical beam paths are provided for purposes of detection or illumination.

12. Device according to claim 1, wherein the STEM detector has one or more than one detection surface, at least one of which captures a principal beam and at least another of which captures scattered electrons.

13. Device according to claim 12, wherein the detection surfaces are located inside, above or at the side of the photo-optical lens.

* * * * *